(12) United States Patent
Yoshii

(10) Patent No.: US 7,254,488 B2
(45) Date of Patent: Aug. 7, 2007

(54) PROBE DESIGNING METHOD AND INFORMATION PROCESSING APPARATUS

(75) Inventor: Hiroto Yoshii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/081,554

(22) Filed: Feb. 22, 2002

(65) Prior Publication Data

US 2003/0008303 A1 Jan. 9, 2003

(30) Foreign Application Priority Data

Feb. 28, 2001 (JP) ............................ 2001-055465
Jan. 31, 2002 (JP) ............................ 2002-023953

(51) Int. Cl.
*G01N 33/48* (2006.01)
(52) U.S. Cl. ...................................................... 702/19
(58) Field of Classification Search .................. 702/19, 702/20
See application file for complete search history.

(56) References Cited

U.S. PATENT DOCUMENTS 4,621,321 A * 11/1986 Boebert et al. ................ 707/8
5,556,749 A 9/1996 Mitsuhashi et al.
6,251,588 B1 * 6/2001 Shannon et al. ............... 435/6

FOREIGN PATENT DOCUMENTS

| JP | 08-317790 | 12/1996 |
| JP | 10-272000 | 10/1998 |
| JP | 11-187900 | 7/1999 |

OTHER PUBLICATIONS

Webster's II New Riverside University Dictionary. Houghton Mifflin Company. 1984, p. 797.*
Predicting DNA duple Stability from the base sequence (Proc. Natl. Acad. Sci. USA vol. 83, pp. 3746-3750, Jun. 1986 Biochemistry).
Kurata K, Nakamura H: "Novel Methods for Primer/Probe Design and Sequence Analysis" Genome Informatics, vol. 11, 2000, pp. 331-332, XP002352345 Tokyo (URL: http://hc.ims.u-tokyo.ac.jp/JSBi/journal/GIW00/GIW00P048.pdf.
Delcher A. L., et al.: "Alignment of whole genomes" Jun. 1, 1999, Nucleic Acids Research, Oxford University Press, Surrey, GB, pp. 2369-2376, XP002281355 ISSN: 0305-1048.
Hosaka N., Kurata K., Nakamura H: "Comparison of Methods for Probe Design" Genomic Informatics, vol. 12, 2001, pp. 449-450, XP002352346 Tokyo (URL: http://hc.ims.u-tokyo.ac.jp/JSBi/journal/GIW01/GIW01P100.pdf).
Kaderali L., et al.: "A new Algorithm for Accelerating Pair-Wise Computations of Melting Temperature" Electronic Notes in Discrete Matehematics, North-Holland, vol. 8, May 2001, pp. 46-49, XP004886768 ISSN: 1571-0653.
Dan Gusfield Ed—Gusfield D.: "Algorithms on Strings, Trees, and Sequences" 1997, Algorithms on Strings, Trees, and Sequences. Computer Science and Computational Biology, New York, Cambridge University Press, US, pp. 263-278, 420, XP002193333 ISBN 0-521-58519-8.

* cited by examiner

*Primary Examiner*—John S. Brusca
*Assistant Examiner*—Jerry Lin
(74) *Attorney, Agent, or Firm*—Cowan, Liebowitz & Latman, P.C.

(57) ABSTRACT

In automatically designing a base sequence to be used as a probe which is hybridized with an unknown nucleic acid fragment to perform gene analysis, a discrimination tree in which a plurality of partial base sequences obtained from target base sequence data are arranged on nodes is generated. The suitability as a probe of a partial base sequence represented by a desired node is evaluated. A plurality of partial base sequences are grouped on the basis of specificity, and an appropriate group combination is selected. A partial base sequence to be used as a probe is determined, from partial base sequences belonging to the selected groups, on the basis of the evaluation result. In this manner, a probe appropriate for analysis can be automatically selected in accordance with a target base sequence to be analyzed. This effectively supports probe designing.

21 Claims, 16 Drawing Sheets

FIG. 3

| DRB1*0101 | GAGCGGGGTGC GGTTGCTGGA AAGATGCATC TATAACCAAG AGGAGTCCGT ... ... |
| DRB1*04011 | GAGCGGGGTGC GGTTCCTGGA CAGATACTTC TATCACCAAG AGGAGTACGT ... ... |
| DRB1*07011 | GAGCGGGGTGC AGTTCCTGGA AAGACTCTTC TATAACCAGG AGGAGTTCGT ... ... |
| DRB1*15011 | GAGCGGGGTGC GGTTCCTGGA CAGATACTTC TATAACCAGG AGGAGTCCGT ... ... |
| ... | ... ... ... |

FIG. 5

| | | | | | |
|---|---|---|---|---|---|
| 1 | GAGCGGGGTGC | GGTTGCTGGA | AAGATGCATC | TATAACCAAG | AGGAGTCCGT ... |
| 2 | AGCGGGGTGC | GGTTGCTGGA | AAGATGCATC | TATAACCAAG | AGGAGTCCGT ... |
| 3 | GCGGGTGC | GGTTGCTGGA | AAGATGCATC | TATAACCAAG | AGGAGTCCGT ... |
| 4 | CGGGGTGC | GGTTGCTGGA | AAGATGCATC | TATAACCAAG | AGGAGTCCGT ... |
| 5 | GGGGTGC | GGTTGCTGGA | AAGATGCATC | TATAACCAAG | AGGAGTCCGT ... |
| .. | | | | | |

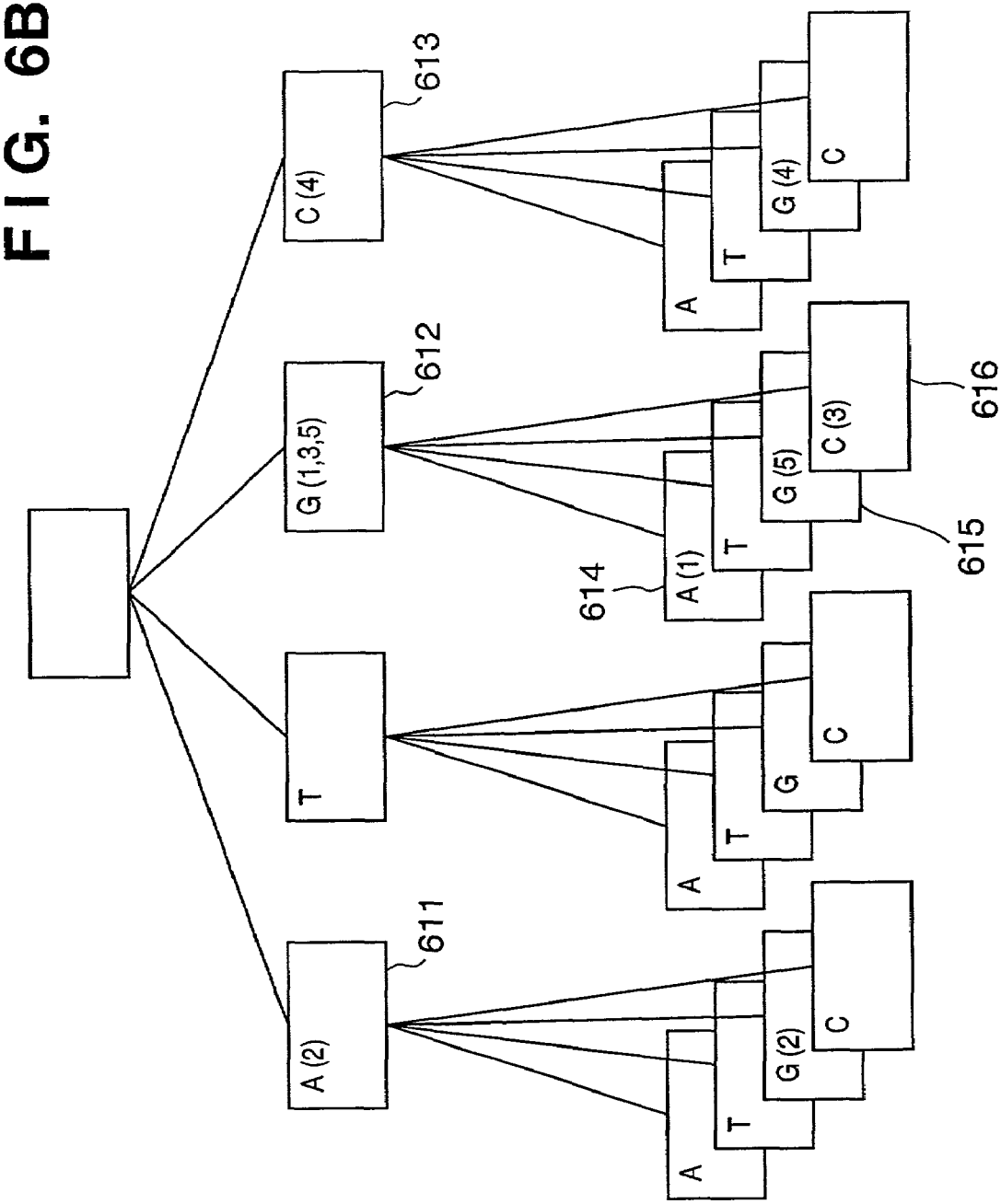

FIG. 7

PARTIAL SEQUENCE CAG REGISTERED IN NODE

| DRB1*0101 | GAGCGGGGTGC GGTTGCTGGA AAGATGCATC TATAACCAAG AGGAGTCCGT | NULL |
| --- | --- | --- |
| DRB1*04011 | GAGCGGGGTGC GGTTCCTGGA CAGATACTTC TATCACCAAG AGGAGTACGT | 21 |
| DRB1*07011 | GAGCGGGGTGC AGTTCCTGGA AAGACTCTTC TATAACCAGG AGGAGTTCGT | 10,37 |
| DRB1*15011 | GAGCGGGGTGC GGTTCCTGGA CAGATACTTC TATAACCAGG AGGAGTCCGT | 21,37 |

FIG. 8

PARTIAL SEQUENCE CAGT REGISTERED IN NODE

| DRB1*0101 | GAGCGGGTGC GGTTGCTGGA AAGATGCATC TATAACCAAG AGGAGTCCGT | NULL |
|---|---|---|
| DRB1*04011 | GAGCGGGTGC GGTTCCTGGA CAGATACTTC TATCACCAAG AGGAGTACGT | NULL |
| DRB1*07011 | GAGCGGGTGC AGTTCCTGGA AAGACTCTTC TATAACCAGG AGGAGTTCGT | 10 |
| DRB1*15011 | GAGCGGGTGC GGTTCCTGGA CAGATACTTC TATAACCAGG AGGAGTCCGT | NULL |

FIG. 12

| DRB1*0101 | GAGCGGGGTGC GGTTGCTGGA AAGATGCATC TATAACCAAG AGGAGTCCGT |
| DRB1*04011 | GAGCGGGGTGC GGTTCCTGGA CAGATACTTC TATCACCAAG AGGAGTACGT |
| DRB1*07011 | GAGCGGGGTGC AGTTCCTGGA AAGACTCTTC TATAACCAGG AGGAGTTCGT |
| DRB1*15011 | GAGCGGGGTGC GGTTCCTGGA CAGATACTTC TATAACCAGG AGGAGTCCGT |
| SPECIFIC BASE POSITION | ----------- -*----*---- *-*-*-**--- -----*----- --------*-- |

PROBE DESIGNING METHOD AND INFORMATION PROCESSING APPARATUS

FIELD OF THE INVENTION

The present invention relates to an information processing apparatus and probe designing method suited to supporting designing of a microarray in which a plurality of nucleic acid probes are arranged.

BACKGROUND OF THE INVENTION

Conventionally, a system for discriminating the expression and sequence of genes by using a DNA microarray has been proposed as disclosed in Japanese Patent Laid-Open No. 10-272000 or 11-187900. In this system, a base sequence fragment (probe) to be hybridized with a sample must be designed beforehand. The characteristic feature of the system is that if a good probe set is designed, a large amount of information can be obtained with respect to a base sequence fragment existing in a sample at a very high probability.

Unfortunately, a wide variety of base sequence fragments can exist in a sample (target) to be analyzed, and they entirely change from one experimental system to another. When that happens, an entirely different probe must be designed. Conventionally, this probe designing is performed by human efforts on the basis of experiments. However, large amounts of base sequences are now beginning to be determined, so it is becoming practically impossible to design probes by human efforts.

SUMMARY OF THE INVENTION

The present invention has been made in consideration of the above situation, and has as its object to automatically select a probe appropriate for analysis in accordance with a target base sequence to be analyzed, thereby effectively supporting probe designing.

According to the present invention, the foregoing object is attained by providing a probe designing method of designing a base sequence to be used as a probe which is hybridized with an unknown nucleic acid fragment to perform gene analysis, comprising: the generation step of generating a tree in which a plurality of partial base sequences obtained on the basis of a target base sequence are arranged on nodes; the evaluation step of evaluating the suitability as a probe of a partial base sequence represented by a desired node, on the basis of partial base sequences indicated by nodes present on that path on the tree, which is connected to the desired node; and the determination step of determining a partial base sequence to be used as a probe on the basis of the evaluation result in the evaluation step.

According to the present invention, the foregoing object is attained by providing a probe designing method of designing a base sequence to be used as a probe which is hybridized with an unknown nucleic acid fragment to perform gene analysis, comprising: the generation step of generating a partial base sequence hash table for typing partial base sequences obtained on the basis of a target base sequence and having a specific length; the evaluation step of evaluating the suitability as a probe of a partial base sequence present in the base sequence hash table, on the basis of the base sequence thereof; and the determination step of determining a partial base sequence to be used as a probe on the basis of the evaluation result in the evaluation step.

According to the present invention, the foregoing object is attained by providing a probe designing method of designing a base sequence to be used as a probe which is hybridized with an unknown nucleic acid fragment to perform gene analysis, comprising: the generation step of generating a discrimination tree for typing a list of a plurality of partial base sequences obtained from target base sequence data; the evaluation step of evaluating the suitability as a probe of a probe candidate present in the discrimination tree; and the selecting step of selecting a probe to be used on the basis of the evaluation result in the evaluation step.

According to the present invention, the foregoing object is attained by providing a probe designing method of designing a base sequence to be used as a probe which is hybridized with an unknown nucleic acid fragment to perform gene analysis, comprising: the generation step of generating a partial base sequence hash table for typing a list of a plurality of partial base sequences obtained from target base sequence data and having a specific length; the evaluation step of evaluating the suitability as a probe of a probe candidate present in the partial base sequence hash table; and the selecting step of selecting a probe to be used on the basis of the evaluation result in the evaluation step.

According to the present invention, the foregoing object is attained by providing an information processing apparatus for realizing the foregoing probe designing method.

According to the present invention, the foregoing object is attained by providing a program for allowing a computer to realize the foregoing probe designing method.

According to the present invention, the foregoing object is attained by providing a storage medium storing a program for allowing a computer to realize the foregoing probe designing method.

According to the present invention, the foregoing object is attained by providing DNA microarray comprising a base probe determined by using the foregoing probe designing method.

According to the present invention, the foregoing object is attained by providing a gene inspecting apparatus comprising a base probe determined by using the foregoing probe designing method.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3 is a view showing an example of base sequence data acquired in step S101;

FIG. 5 is a view showing partial base sequences (probes) obtained from a target base sequence;

FIG. 6B is a view showing the contents of each node of the discrimination tree;

FIG. 7 is a view showing a partial base sequence registered in a certain node on the discrimination tree;

FIG. 8 is a view showing a partial base sequence registered in a certain node on the discrimination tree;

FIG. 12 is a view for explaining specific base positions in a target according to the second embodiment;

DETAILED DESCRIPTION OF THE PREFERRED EMBODIMENTS

Preferred embodiments of the present invention will now be described in detail in accordance with the accompanying drawings.

First Embodiment

[Outlines of Apparatus and Operation]

In the following embodiment, a probe designing method which designs, by using a computer, an optimum oligonucleotide probe for use in a nucleic acid sequence analyzing system using a so-called DNA microarray, and an apparatus for executing the method, will be explained.

Figure 2:
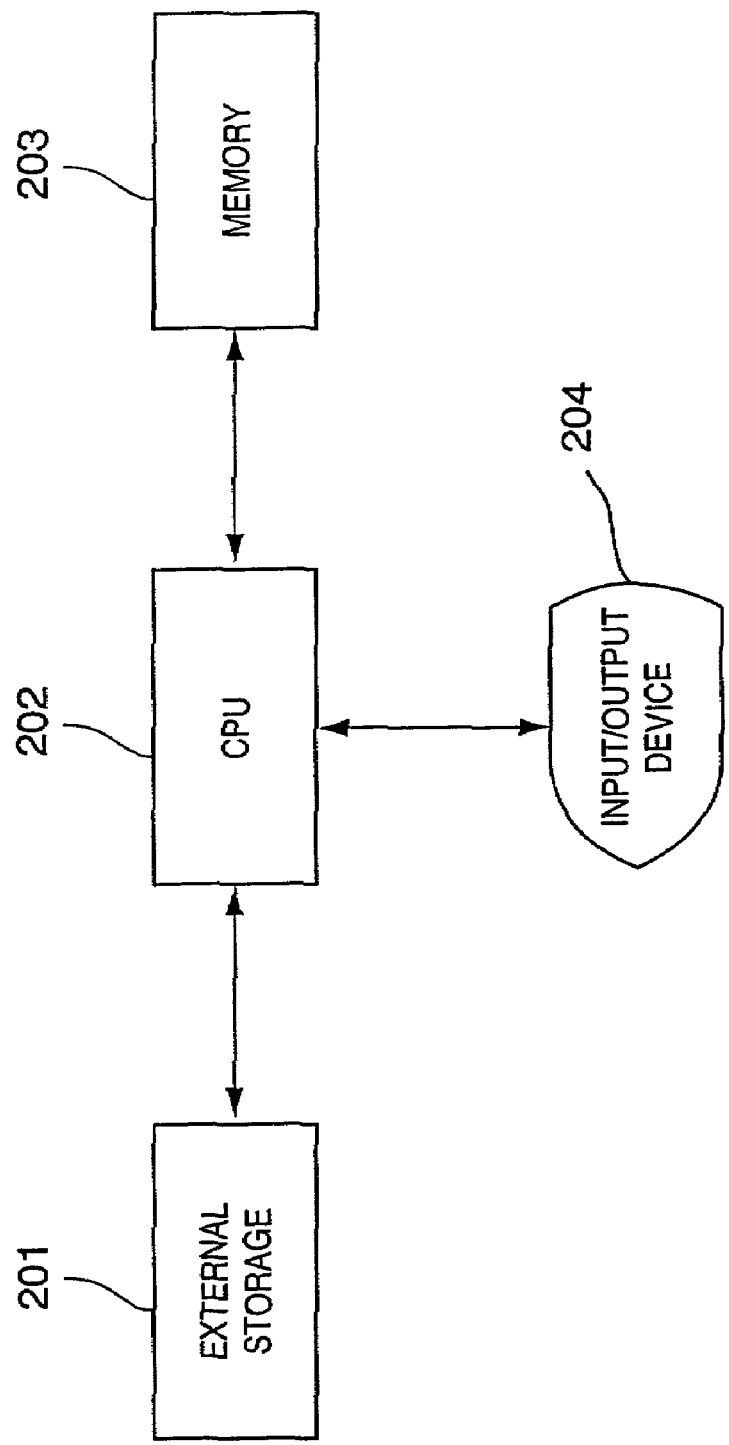
FIG. 2 is a block diagram showing the arrangement of an information processing apparatus to which the probe designing method of the first embodiment is applied.

FIG. 2 is a block diagram showing the arrangement of an information processing apparatus to which the probe designing method of this embodiment is applied. In this embodiment, an information processing apparatus comprising an external storage 201, a central processing unit (CPU) 202, a memory 203, and an input/output device 204 executes the probe designing method explained below. An example of the information processing apparatus having this configuration is a personal computer.

The external storage 201 stores a program for implementing the probe designing method of this embodiment, base sequence data of targets, and parameters. This external storage 201 is also used to store probe sequences derived by this embodiment. The CPU 202 executes the probe designing program and controls all the devices.

The memory 203 temporarily stores the program to be executed by the CPU 202, subroutines, and data. The probe designing method control program stored in the external storage 201 is loaded into the memory 203 and executed by the CPU 202. The input/output device 204 interacts with the user. In many cases, the user issues, via this input/output device, a trigger for executing the program for implementing the probe designing method explained below. Also, the user checks the results and controls the program parameters via this input/output device.

Figure 1:
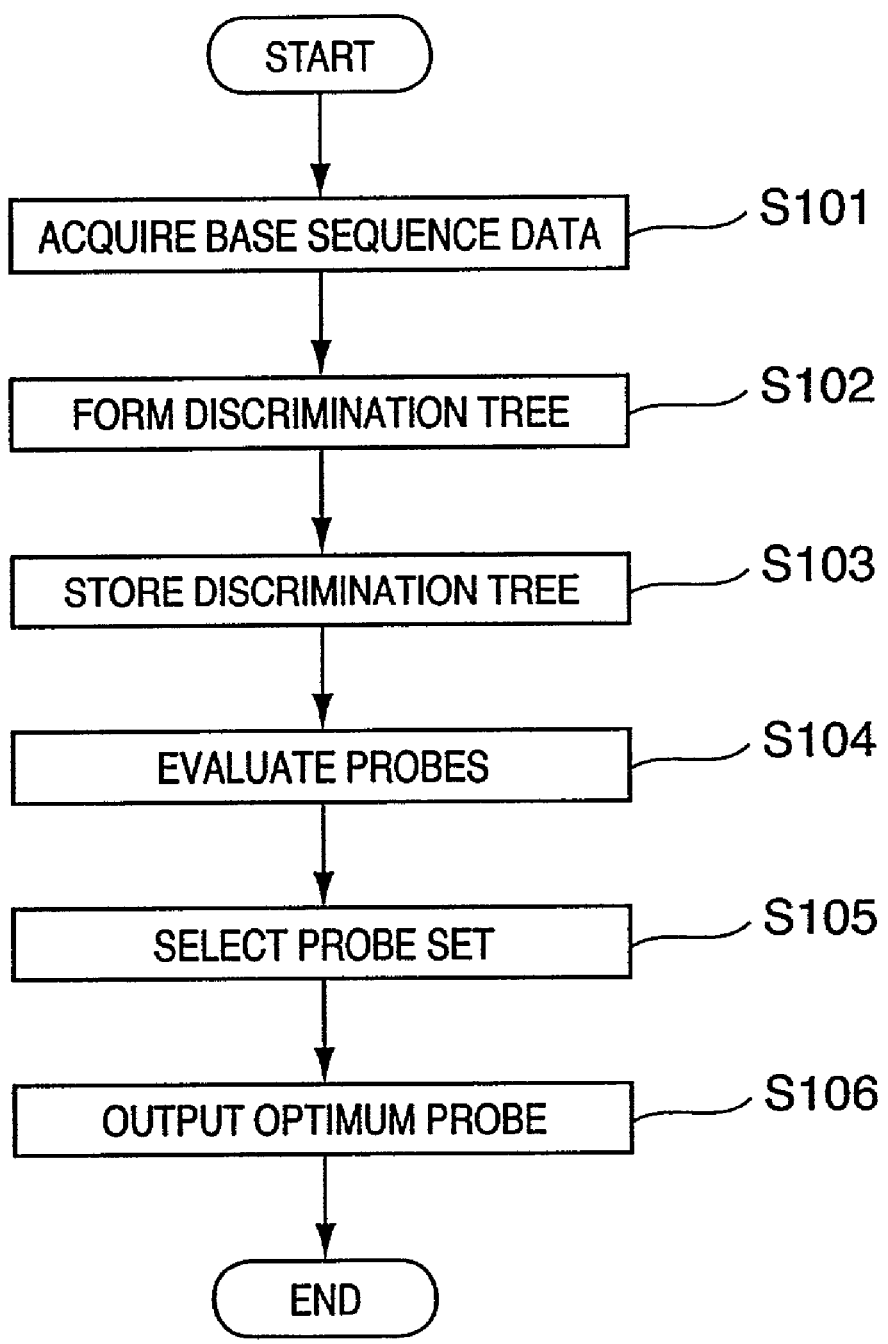
FIG. 1 is a flow chart for explaining the procedure of a probe designing method according to the first embodiment.

FIG. 1 is a flow chart for explaining the procedure of the probe designing method according to the first embodiment. An outline of the probe designing method procedure of this embodiment will be explained. First, in step S101, base sequence data of a target is acquired from the external storage 201. In step S102, a discrimination tree is formed on the basis of the base sequence data acquired in step S101. This discrimination tree and its formation will be described later. In step S103, the discrimination tree formed in step S102 is stored in the external storage 201.

In step S104, the discrimination tree stored in step S103 is used to evaluate each probe (partial base sequence) expressed on the tree. That is, evaluation for selecting a probe candidate most adequate as a probe, from probe candidates present on the discrimination tree, is performed. In step S105, an optimum probe set as a final outcome is selected on the basis of the evaluation result. In step S106, the optimum probe is output. Examples of the output destination are the external storage 201 and a display device or printer included in the input/output device 204.

Each process will be described in detail below.

[Generation of Discrimination Tree (Steps S101-S103)]

FIG. 3 is a view showing an example of the base sequence data acquired in step S101. This base sequence information shown in FIG. 3 is a part of genes called HLA or MHC. Genes relevant to human antibody generation are coded in this portion, and the portion changes from one person to another. This means that there is a base sequence similar to but not identical with that shown in FIG. 3. As to this HLA, 100 or more human gene types are confirmed. If these types are different, fatal rejection is highly likely to occur in transplantation between different individuals. At present, DNA sequencing is performed for a patient and an organ donor to completely determine base sequences, thereby typing this HLA. This operation can be performed easily and rapidly by the use of an appropriate DNA microarray.

Figure 4:
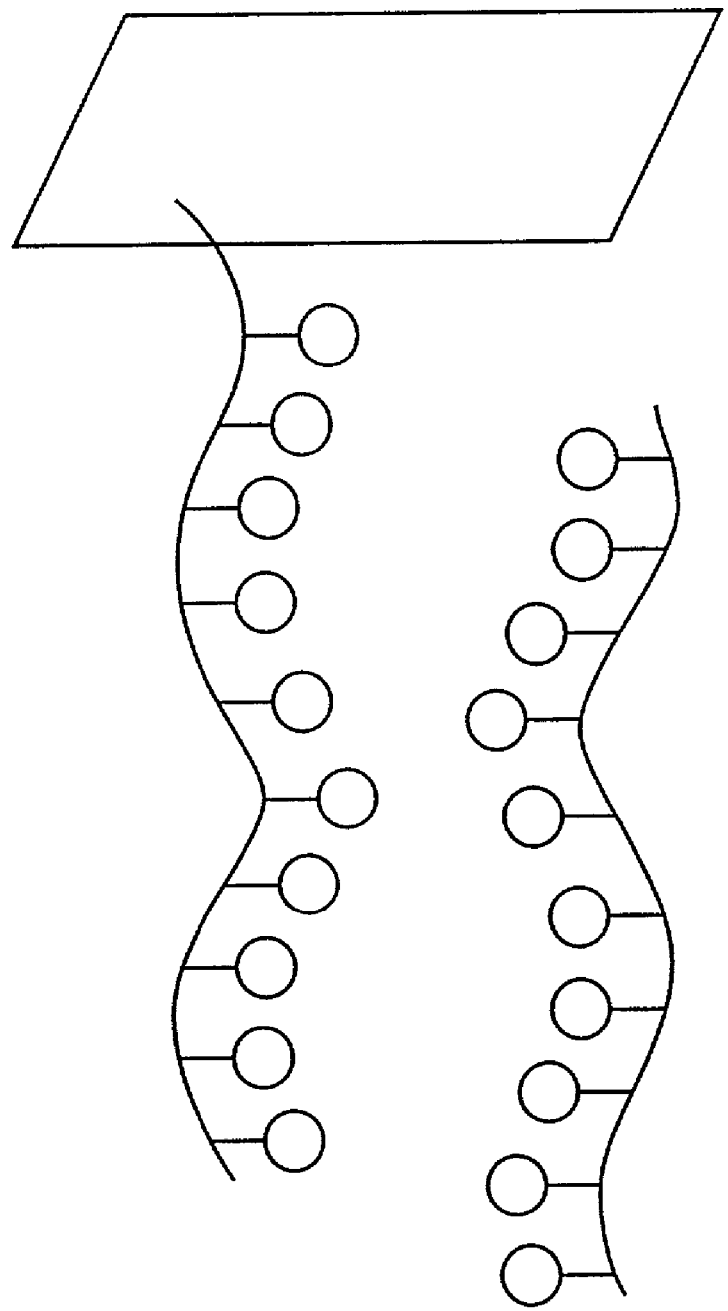
FIG. 4 is a view showing hybridization on a DNA microarray.

FIG. 4 is a view showing hybridization on a DNA microarray. In vivo, a DNA base sequence has a double-helix structure in most cases, and these two chains are bonded by hydrogen bonds between bases. On the other hand, an RNA base sequence often exists as a single chain. DNA has four types of bases, i.e., ACGT, and RNA also has four types of bases, i.e., ACGU. Base pairs capable of forming hydrogen bonds are A-T(U) and G-C pairs. In the following explanation, the formation of a probe pertaining to a DNA base sequence will be described.

Hybridization is a process in which single-stranded base sequence molecules partially bind via a complementary base sequence in a certain portion, thereby forming two chains. A reaction assumed in this embodiment is that the upper base sequence (probe sequence) attached to a substrate in FIG. 4 is shorter than the lower base sequence molecules in a sample. Accordingly, if base sequence molecules present in the sample contain the probe sequence, this hybridization reaction is successful; the target base sequence molecules in the sample are trapped.

However, hybridization is possible not only when all regions of a probe sequence are complementary. That is, even if there is a portion where no pair is formed, target base sequence molecules are sometimes trapped. Especially when a base only at the end portion of a probe cannot be bonded, hybridization is highly likely to occur, so a target base sequence cannot be accurately chosen. Therefore, a probe sequence set different only at its end portion is inadequate for experiments using hybridization. More specifically, a base sequence which contains a sequence different from a target base sequence in its central portion is preferred. Also, the intensity of a hybridization reaction increases as the length of a probe base sequence increases. Accordingly, it is ideal to select, as probe sequences arranged on a DNA microarray, base sequences having similar hybridization intensities, i.e., close to each other in number of bases contained.

As described above, a probe base sequence as a final output must be a base sequence complementary to a partial sequence in a sample. In this embodiment, therefore, all partial base sequences are prepared beforehand in the discrimination tree formation process in step S102. This is illustrated in FIG. 5.

FIG. 5 is a view showing partial base sequences (probes) obtained from a target base sequence. These base sequences shown in FIG. 5 are some partial sequences of a sequence of type DRB1*0101 shown in FIG. 3. As shown in FIG. 5, entirely different partial base sequences are obtained by shifting the end portion base by base. All these sequences are sequence candidates for hybridization with a probe. If an object sequence of a certain type has n bases, n−1 partial base sequences exist as a whole for that sequence. In this embodiment, a discrimination tree which types all partial base sequences is generated. However, it is also possible to set a predetermined number of depths in advance and generate a discrimination tree for partial base sequences having a predetermined number of bases or more.

Figure 6A:
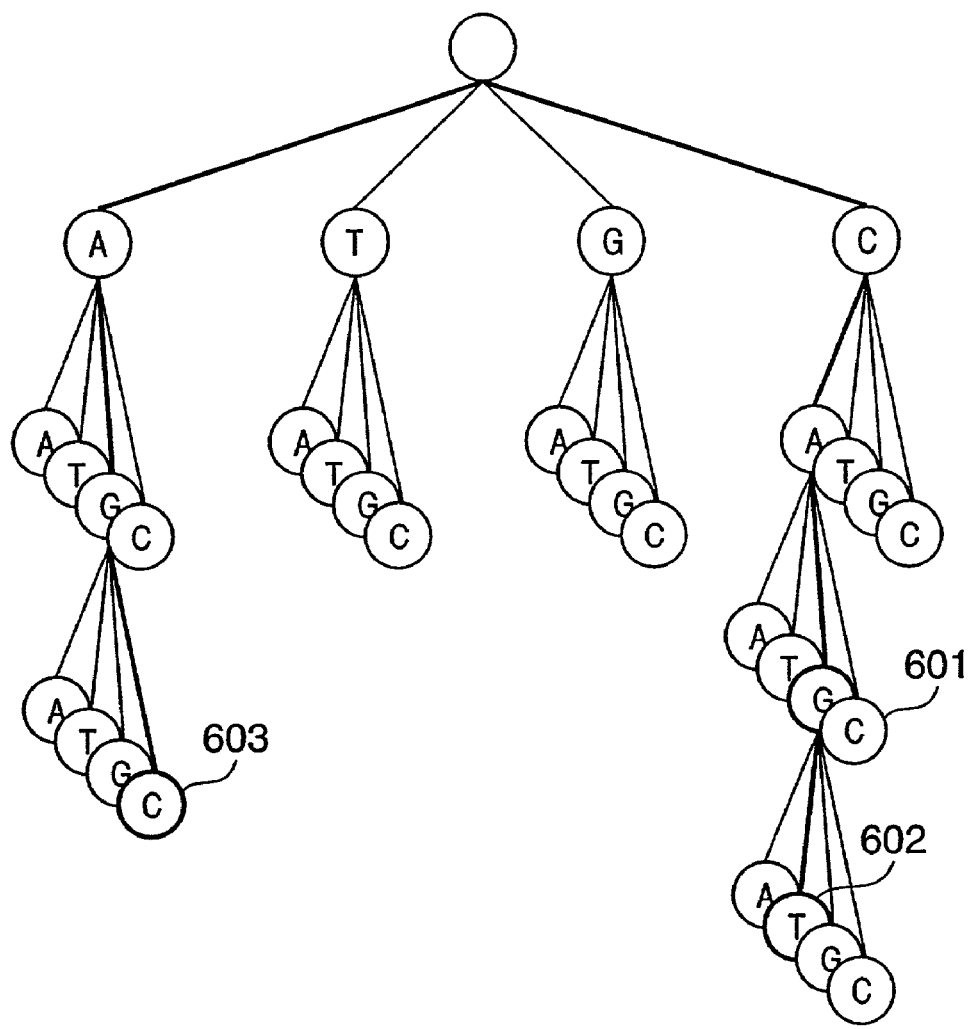
FIG. 6A is a view for explaining a discrimination tree according to the first embodiment.

Next, a discrimination tree for discriminating/typing all these partial sequences is formed. FIG. 6A is a view for explaining this discrimination tree. Each of all nodes configuring the tree has four child nodes (A, T, G, and C). For each of these four child nodes, the base sequence of a position of interest is typed by one of ATGC. As the simplest example, a method of shifting the position of interest one by one will be explained below.

FIG. 6B is a view showing the typing of partial base sequences to the individual nodes of the discrimination tree. At a root node, the base sequence at the left end of each partial base sequence is checked. Each partial base sequence is typed in accordance with the type of base. For example, if a base sequence is derived from DRB1*0101 of HLA shown in FIG. 5, a partial base sequence of No. 2 in FIG. 5 is typed to a node 611 of A, partial base sequences of Nos. 1, 3, and 5 are typed to a node 612 of G, and a partial base sequence of No. 4 is typed to a node 613 of C. The partial sequences of Nos. 1, 3, and 5 are further typed by deeper nodes. More specifically, the next node of the partial base sequence of No. 1 is A, the next node of the partial base sequence of No. 3 is C, and the next node of the partial base sequence of No. 5 is G. Accordingly, these partial base sequences are stored in nodes 614, 615, and 616.

By the above processing, all partial base sequences of all targets are registered in individual nodes to form a discrimination tree. In this discrimination tree formation process, a discrimination tree for discriminating whole data expanded into partial sequences as shown in FIG. 5 is formed. Therefore, an arbitrary partial base sequence is registered somewhere on the formed discrimination tree. When the discrimination tree is formed by the method by which the position is shifted one by one from the left as described above, the left-hand side of the registered base sequence can be revealed by tracing nodes, in which a certain partial base sequence is registered, back to the root node.

FIGS. 7 and 8 are views each showing a partial base sequence registered in a certain node on the discrimination tree. Assume, for example, that the base sequence composed of fifty bases of four types shown in FIG. 3 is contained in a sample. When nodes are traced in the order of CAG in the discrimination tree shown in FIG. 6A, information indicated on the right-hand side of the table shown in FIG. 7 is stored in a node 601 of FIG. 6A. That is, this node 601 stores DRB1*0101.. "NULL", DRB1*04011 . . . "21", DRB1*007011 . . . "10,37", and DRB1*15011 . . . "21,37". This information indicates that no partial base sequence CAG exists in DRB1*0101 (NULL), and CAG exists in the 21st position in DRB1*04011, in the 10th and 37th positions in DRB1*07011, and in the 21st position in DRB1*15011.

FIG. 8 shows the contents of a node of T of child nodes connected to the node shown in FIG. 7, i.e., the contents of a node 602 in FIG. 6A. A partial base sequence corresponding to this node 602 is CAGT, and the only partial sequence matching this is the 10th partial sequence in DRB1*07011.

In the above example, the type of base is analyzed at a position shifted one by one from the left, so the node order matches the base sequence. However, this position can also be changed in accordance with an algorithm. In a hybridization reaction, the difference between central base sequences is important. In the formation of a discrimination tree, therefore, one effective method is to rearrange nodes so as to shift the base sequence position of interest from the center to the perimeter.

For example, in this method a node corresponding to a partial base sequence of C→A→G from the left in FIG. 7 is analyzed as "A in the middle"→"G at the right"→"C at the left". In this case, a node is analyzed not one by one from the left but in the order of middle, right end, and left end. Accordingly, when the method of analyzing a node from the left is used, the node 601 in FIG. 7 is present in a position {root node→node of C→node of A→node of G}. However, when the method of analyzing a node from the center to the perimeter, this node 601 is present in a position {root node→node of A→node of G→node of C}. This means that when the position of a base sequence (in the above example, CAG) of interest changes, the node 601 changes to a node 603 (A→G→C) in FIG. 6A. In this case, not the node 601 alone but the structure of the whole discrimination tree changes.

A general example of the above-mentioned rearrangement is to configure a discrimination tree by rearranging nodes in the order of "a, a+1, a−1, a+2, a−2, . . . ," when the number of base sequences is n, (n+1)/2 is $\underline{a}$ if n is an odd number, and n/2 is $\underline{a}$ if n is an even number. It is of course also possible to analyze a node in the order of center, left end, and right end.

As described above, a discrimination tree is formed by the discrimination tree formation process. It should be noted that the number of nodes increases exponentially. Therefore, computer resources become insufficient if nodes are not saved. More specifically, processing is necessary by which if no more base sequence corresponding to a node exists in an assumed sample (target), the expansion of child nodes of that node is stopped. When a certain depth is exceeded by this processing, the node increase becomes steady. For example, when the number of types of base sequences to be discriminated is T and the number of partial sequences of each of these base sequences is N, only T×N nodes increase even in the worst case.

[Probe Evaluation Method (Step S104)]

The probe evaluation process (S104) shown in FIG. 1 will be explained below. Each of all nodes of the discrimination tree described above is obtained by coding any partial base sequence which can exist in a sample. Therefore, all nodes of the discrimination tree can be probe candidates. However, partial base sequences which effectively function as probes are limited owing to the conditions of a hybridization reaction. The probe evaluation process explained below evaluates a node as a probe.

First, probes placed on a chip preferably has as close hybridization intensities as possible. Accordingly, a method of determining the number of probe base sequences in advance is usable. In this method, only nodes at a certain depth of the discrimination tree are probe candidates. It is of course also possible to narrow down to fewer probe candidates by giving some margin to the number of base sequences. In this case, nodes within the range from a certain depth to another certain depth are probe candidates.

Strictly speaking, hybridization intensity changes even for the same number of base sequences. As a method of calculating this, "Oligoribonucleotide/Oligodeoxyribonucleotide Complimentary Base Pair Structure Stability Analyzing Method" is proposed in Japanese Patent Laid-Open No. 8-317790. When a base sequence is determined, this method can estimate the hybridization intensity of the base sequence. Accordingly, it is possible to estimate the hybridization intensity of each node from a base sequence corresponding to that node and, on the basis of these estimated values, to narrow down probe candidates to nodes on the discrimination tree. Note that in this method, the melting temperature of the base sequence of each node on the discrimination tree is calculated by, e.g., the method described in "Predicting DNA duple stability from the base sequence" (Proc. Natl. Acad. Sci. USA Vol. 83, pp. 3746-3750, June 1986 Biochemistry).

One superior advantage of this embodiment is that the discrimination tree codes a partial base sequence having an arbitrary length, so the process of selecting probe candidates having lengths within a certain range or having melting temperatures within a certain range can be performed at very high speed.

A probe containing all partial sequences having a certain specific length (e.g., 20 bases) can be designed by the above-mentioned narrowing. However, partial base sequences contained in all targets have no specificity, so this probe is meaningless. That is, even if this probe is used to perform a hybridization reaction with each target, no information can be obtained. Therefore, it is necessary to measure the specificity of a partial base sequence specified by a node of the discrimination tree. Entropy is generally used as a scale of this specificity.

For example, assuming that the number of base sequence types as targets is t and the numbers of partial base sequences of these t types contained in a certain node are N1, N2, N3, . . . , Nt, the entropy of this node is calculated by $$\text{entropy} = \frac{1}{\sum_{i=1}^{t} N_i} \cdot \sum_{i=1}^{t} \left[ N_i \left\{ \log\left(\sum_{i=1}^{t} N_i\right) - \log(N_i) \right\} \right] \quad (1)$$

It is of course also possible to measure the specificity of a base sequence by a method other than entropy herein explained.

Figure 9:
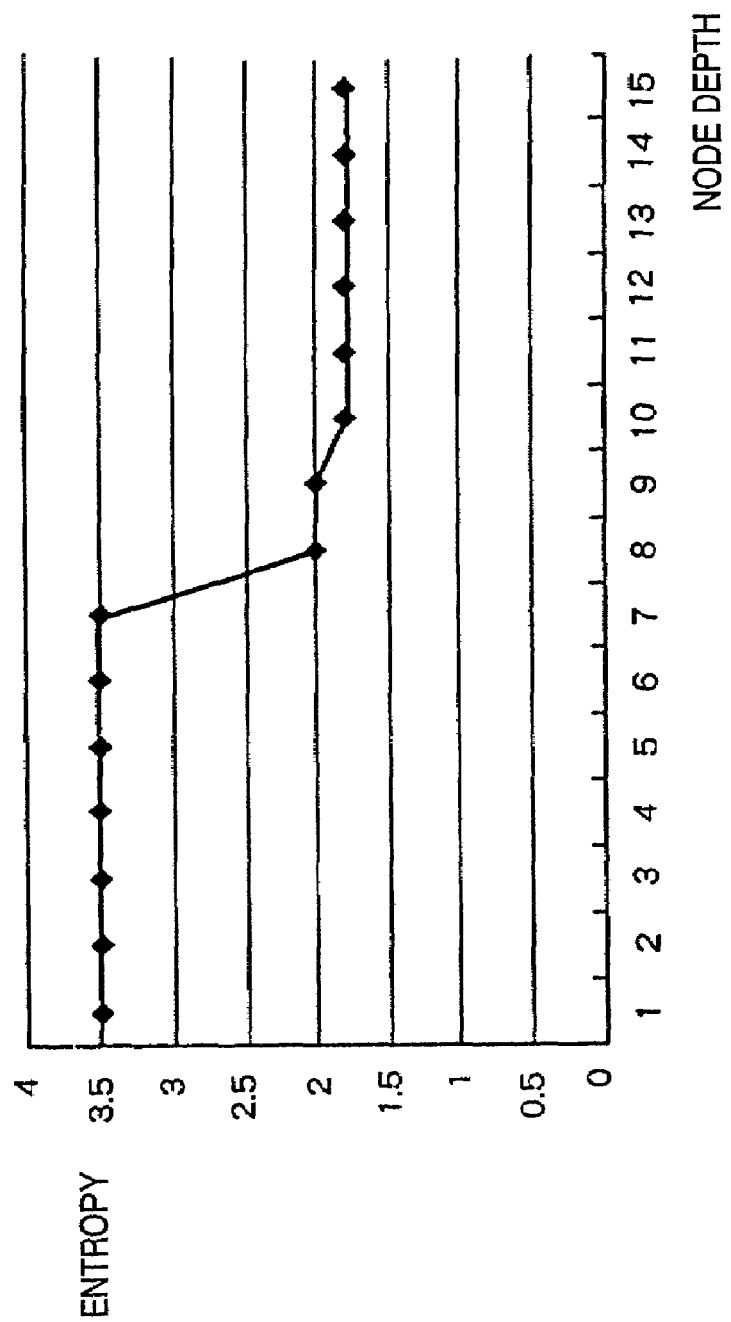
FIG. 9 is a graph showing the transition of entropy typically optimum as a probe.

A method of finding an optimum probe by using the entropy calculated by the above equation will be described below. FIG. 9 is a graph showing the transition of entropy typically optimum as a probe. The abscissa of this graph indicates the node depth. In this example, the results of checking of base sequences having a length of 15 bases are shown. The entropy normally decreases when nodes of the discrimination tree are traced. For example, the specificity of the node 602 is higher than that of the node 601 in FIG. 6A, and the entropy decreases. Assuming that the nodes 601 and 602 in FIG. 6A hold the partial base sequence sets as shown in FIGS. 7 and 8, respectively, the node 602 corresponds to a partial sequence unique to DRB1*07011, and the entropy is 0.

In the graph shown in FIG. 9, the entropy decreases at the positions of the eighth and tenth bases. That is, this graph shows that the eighth and tenth partial base sequences coded by this node are base sequences unique to a certain type set. As shown in FIG. 9, a node having an abrupt entropy decrease near the center is an optimum probe.

One superior advantage of this embodiment is that this entropy decrease can be automatically analyzed by tracing nodes in the direction of depth and, on the basis of this analysis, a probe having base specificity in a central position can be reliably chosen.

A practical probe evaluation function for realizing the probe selecting process as described above can be the one by which the score is high if an entropy decrease is present in a central position. As an example, it is possible to use an evaluation function indicated by Evaluation score=(entropy decrease)*(1/(distance from central position+1))$^n$ (2)

In this method, however, the length of a probe must be presumed beforehand because the central position cannot be determined unless the total length of the probe is determined.

An example of a method of performing evaluation without limiting the length of a probe beforehand is the method, already described in the discrimination tree formation step, which analyzes base variations from the center to the perimeter. When a discrimination tree is formed by this method, an abrupt entropy decrease preferably exists at the beginning of the discrimination tree, so an evaluation function corresponding to this is prepared.

For example, it is possible to use an evaluation function indicated by

Evaluation score=(entropy decrease)*(1/(distance from root node))$^n$ (3)

This method can control designing of a probe having an arbitrary length.

Probe evaluation is performed by introducing the evaluation function as described above, and the evaluation value is stored in each node.

Figure 10:
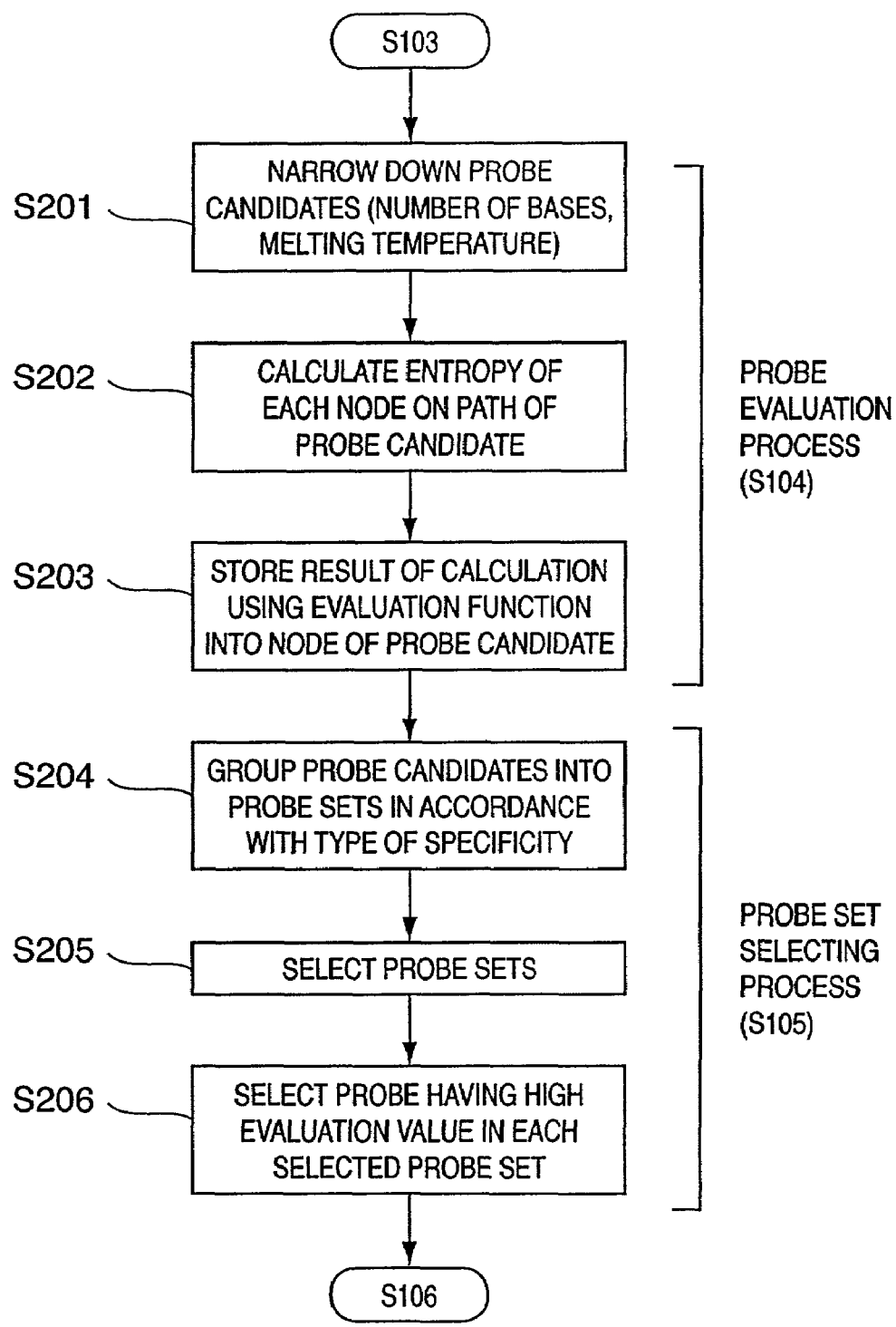
FIG. 10 is a flow chart showing details of a probe evaluating process (step S104) and a probe set selecting process (step S105) according to the first embodiment.

FIG. 10 is a flow chart showing details of the probe evaluation process (step S104) and the probe set selecting process (step S105) of this embodiment. In step S201, as described above, probe candidates are narrowed down to fewer probe candidates the discrimination tree by the number of bases (node depth) or by the melting temperature based on a base sequence. In step S202, the entropy is calculated by equation (1) for each node, on a path on the tree, of each probe candidate obtained by the narrowing, and stored in that node. In step S203, evaluation values are calculated by using the evaluation function indicated by equation (2) or (3) for the nodes of these probe candidates, and stored in these nodes.

Referring to FIG. 10, the probe evaluation using the evaluation function is performed for probe candidates obtained by extracting partial base sequences having a predetermined length or within a predetermined length range, or for probe candidates having melting temperatures within a predetermined range. However, it is also possible to perform the evaluation for all probes on the discrimination tree and narrow down these probes to fewer probes by a predetermined length range or a predetermined melting temperature range in the probe set selecting process explained below.

[Probe Set Selecting Process (Step 105)]

The probe set selecting process (step S105) shown in FIG. 1 will be described below. Steps S204 to S206 in FIG. 10 indicate the procedure of this probe set selecting process. If necessary, probe candidates are extracted, and inadequate probes are excluded. The above-mentioned probe evaluation step evaluates probe candidates obtained by selecting only probes within a certain length range or a certain melting temperature range. However, this determination can also be performed in this probe set selecting step. When this is the case, the probe evaluation in steps S202 and S203 mentioned above is performed for all probes on the discrimination tree.

In step S204, a set of base sequences as probe candidates is divided into a plurality of subsets, in order to prevent a redundant probe set from being chosen. Information indicating the specificity of a probe can be expressed by a bit string which indicates whether the probe is contained in individual base sequence types. For example, if t base sequence types are present, the specificity of a probe can be expressed by t-bit information. Assuming that a bit is set to 1 if a base sequence type contains a probe and set to 0 if not, a probe contained in all base sequence types is expressed by the value of t bits all of which are 1. When probes having different t-bit strings are divided into different groups, subsets each reflecting the specificity of a probe are formed. All probes included in the same subset by this processing have the same type of specificity and have the same function as a probe in terms of information. Accordingly, probes given high evaluation values in the aforementioned probe evaluation can be selected from subsets of individual types and used in a microarray. In this embodiment, however, further narrowing is performed by using this probe set as a unit.

When the base sequences of probe candidates are divided into a plurality of subsets as described above, unnecessary subsets can be removed from these subsets. When this processing is performed, a necessary and satisfactory independent probe set is formed. This processing will be explained below by presenting its practical example.

Assume that base sequence types as targets are A, B, C, and D. If base sequences as probe candidates are divided into five subgroups in accordance with their specificities, the specificity of each subgroup can be expressed by the value of the four bits described previously. Assume that the specificities of these five subgroups are represented by bit strings 1010, 1100, 0001, 1110, and 0111. In this case, it is actually well possible to determine the four types by the first two subgroups (1010 and 1100) in terms of information.

Letting $\alpha$ and $\beta$ denote probes selected from the first two subgroups, hybridization occurs in both $\alpha$ and $\beta$ if the sample is a base sequence of type A. Likewise, if the sample is B type, hybridization occurs not in $\alpha$ but only in $\beta$; if the sample is C type, hybridization occurs not in $\beta$ but only in $\alpha$; and if the sample is D type, no hybridization occurs in either $\alpha$ or $\beta$.

If the experiment is completely controllable and if information indicating whether the hybridization reaction occurs is obtained at a very high probability, probes included in the first and second subgroups are necessary and satisfactory as base probes for discriminating between the four types A, B, C, and D as targets. From an information viewpoint, the first and second subgroups are independent, and the third, fourth, and fifth subgroups belong to the information space generated by these first and second subgroups. Strictly speaking, therefore, probe candidates belonging to the third, fourth, and fifth subgroups are unnecessary.

Note that the process of selecting these necessary and satisfactory independent subsets is very time-consuming. Also, it is in practice often necessary to select a final probe set with redundancy to some extent for the following reason. That is, unlike data handled by a computer, data obtained as a result of a reaction of a living substance is highly likely to entrap a large amount of noise during the experiment. If, therefore, only minimum necessary probe sets are prepared, no accurate experimental results can be reproduced if the amount of noise is large. Accordingly, it is practically often unnecessary to select only necessary and satisfactory independent subsets as described above.

In step S205, probe sets are selected as above, and subsets of probe candidates as objects are finally obtained. Of these selected subsets, probes having high evaluation values obtained in the probe evaluation step are selected as a final probe set. In this embodiment, a base sequence obtained by the above procedure has the order of partial base sequences extracted from the base sequence of a target. In step S106, therefore, the selected partial base sequence is converted into a complementary base sequence before being output. For example, if a partial base sequence "GAGCG" is selected in step S105, "CTCGC" is output as a corresponding probe in step S106. It is of course also possible to use a base sequence complementary to the base sequence of a target in the formation of a discrimination tree in step S102. In this case, the base sequence of a probe selected in step S105 is directly output in step S106.

By the use of a probe selected as above, an oligonucleotide probe optimum for a DNA microarray system can be designed. Consequently, more accurate gene expression information and individual identification information can be obtained.

Note that various modifications can be made from the evaluation explained in the above embodiment. For example, the process can be simplified such that if a value calculated by the evaluation function exceeds a predetermined value, a partial base sequence corresponding to the node is immediately determined as a probe. Alternatively, the process can be simplified such that a partial base sequence having a portion in which a change in the entropy calculated by equation (1) exceeds a predetermined value is determined as a probe.

Second Embodiment

In the first embodiment, a discrimination tree is generated for probe selection, and probe evaluation is performed on the basis of this tree. In the second embodiment, a hash table is used instead of the discrimination tree. Note that the apparatus configuration is the same as the first embodiment (FIG. 2), so a detailed description thereof will be omitted.

Figure 11:
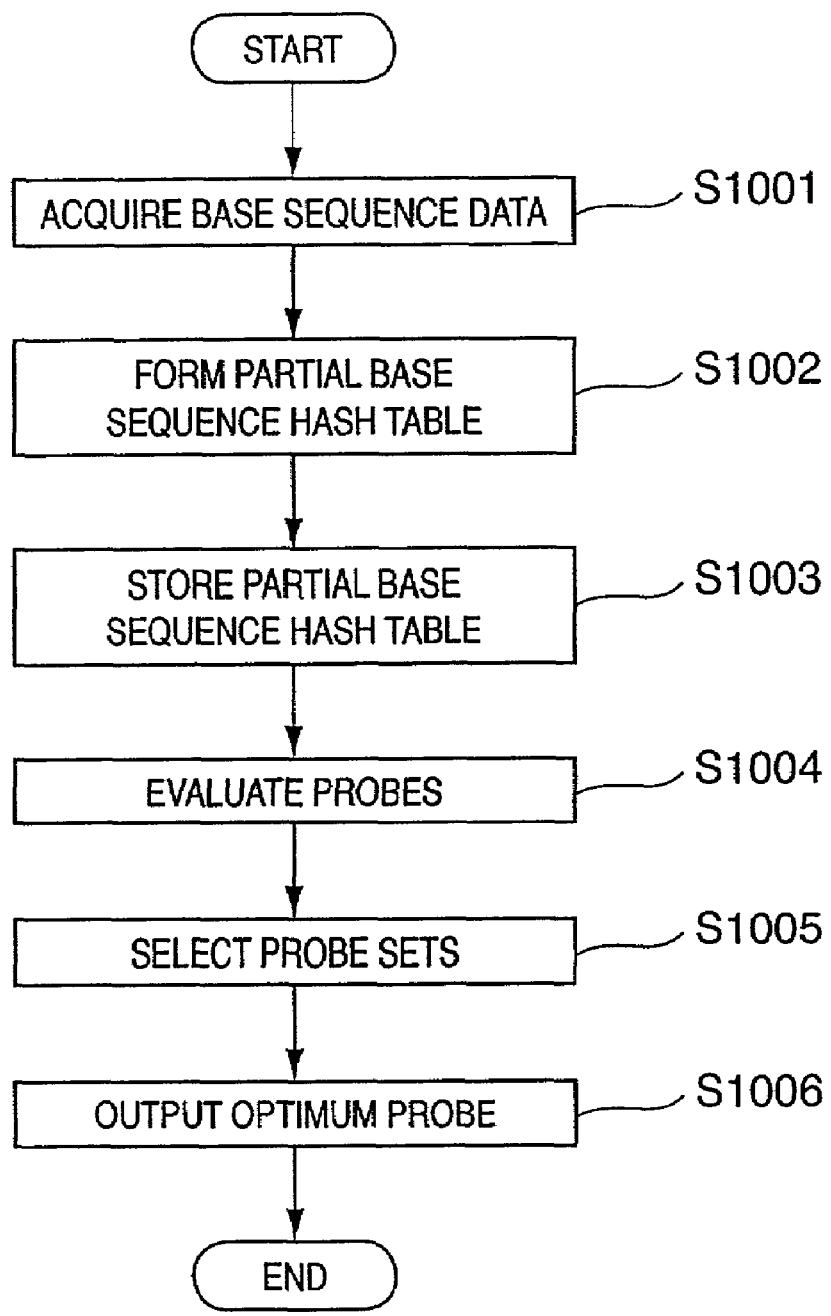
FIG. 11 is a flow chart for explaining the procedure of a probe designing method according to the second embodiment.

FIG. 11 is a flow chart for explaining the procedure of a probe designing process according to the second embodiment. In step S1001, target base sequence data is acquired. In step S1002, a partial sequence hash table which types partial base sequences, within a certain length range, contained in the acquired base sequence data is formed. In step S1003, this partial base sequence hash table formed in step S1002 is stored in an external storage 201.

In step S1004, a probe evaluation process is executed to evaluate whether each probe candidate present in the partial base sequence table is adequate as a probe. In step S1005, probe set selection is performed to select an optimum probe as a final outcome on the basis of the probe evaluation results. In step S1006, the optimum probe obtained as a final outcome is output. In this processing, the input is target base sequence data, and the output is a probe suited to be mounted on a microarray.

[Generation of Partial Base Sequence Hash Table (S1003 & S1004)]

In the second embodiment, a partial base sequence hash table is formed instead of the discrimination tree explained in the first embodiment. This is equivalent to forming nodes at a certain depth of the discrimination tree. A hash table is a method very often used as a software technology. This method saves information strings capable of having a large amount of variations in a compact form.

For example, consider how partial base sequences having a length of 20 bases are contained in a target base sequence. Variations which 20-base base sequences can take are theoretically $4^{20}$ (=40 bits), and it is practically impossible to prepare a large space like this. On the other hand, variations of base sequences which can exist in a sample are extremely few compared to this 40-bit space. Accordingly, 20-base partial base sequences are coded into 40-bit values, and these values are divided by, e.g., a sufficiently large prime number. In this manner, these 20-base partial base sequences can be accommodated into a compact space practically having no duplication. This method is called a data storing/arranging method using a hash table. If duplication occurs although base sequences are actually different, it is possible to prepare two hash tables or store data in the next address of a hash table.

When all partial sequences having a specific length in a target base sequence are thus stored and arranged by using a hash table, the type and position of base sequence in which these partial sequences are contained can be automatically specified. This is the same as the state in which the left column in FIG. 7 or 8 is registered in each entry of a hash table. Consequently, all pieces of node information at a certain depth of the discrimination tree in the first embodiment are obtained.

Performing this operation for partial base sequences having a plurality of lengths is equivalent to expanding nodes from a certain depth to another certain depth in the first embodiment. As described in the first embodiment, in designing a probe within a certain length range or a certain melting temperature range, all probe candidates are obtained by the above processing.

[Evaluation of Probe Candidates (S1004)]

Next, probe evaluation for determining whether these probe candidates are adequate as probes will be explained below. The second embodiment decisively differs from the first embodiment in this probe evaluation process. The second embodiment is slightly inferior in performance to the first embodiment. That is, the first embodiment is in many instances capable of designing higher-performance probes. However, the second embodiment is superior in the simplicity and rapidness of processing to the first embodiment. This gives the second embodiment a high value of use.

As stated in the first embodiment, the quality of a probe increases if the specificity of the base sequence of the probe is present in its central portion. Therefore, it is desirable to check the specificity in this central portion. However, this check is very difficult to perform because, unlike the first embodiment, no partial information in the base sequence is available. In the second embodiment, therefore, specificities (called specific base positions) present in a target base sequence are obtained beforehand. This is shown in FIG. 12.

Specific base positions are indicated in the lowermost row of the table shown in FIG. 12. Locations having * marks are portions where not all bases of the target base sequence are common, i.e., locations (specific base positions) having specificity between certain types. A probe candidate containing this position in its center is a good probe. The quality of each probe candidate is evaluated by using a function which evaluates the location of this specific base position in a probe candidate.

More specifically, a probe candidate can be evaluated using an evaluation function indicated by $$\text{Evaluation score} = \Sigma\{(1/(\text{distance of specific base position from central position}+1)\}^n \quad (4)$$

In the above example, a specific base position is evaluated by two values, i.e., whether or not specificity exists. However, a specific base position can also be evaluated by continuous values by using a scale such as entropy as explained in the first embodiment. For example, portions having * marks in FIG. 12 are called specific base sequences. In some of these locations, most types are G and only one type is A (the entropy decrease is small); in some other locations, half types are G and the other half types are A (the entropy decrease is large). As described previously, discrimination is advantageously performed if a location having a large entropy decrease is present in the center. Therefore, weighting is so performed for equation (4), e.g., an entropy decrease at the position of a specific base sequence is integrated to equation (4). This allows more accurate evaluation of prove candidate quality.

[Probe Set Selecting Process (S1005)]

The probe set selecting process executed in step S1005 is the same as the first embodiment (step S106), so a detailed description thereof will be omitted.

In the second embodiment as described above, probe candidates are selected using a hash table. This increases the simplicity and rapidness of the processing.

As has been described above, by placing on a substrate a base probe obtained in accordance with the probe designing process of the first or second embodiment, a DNA microarray containing a base probe suited to typing a target is obtained. Note that when a base probe is determined, a DNA microarray suitable for a predetermined target can be manufactured using a known DNA microarray manufacturing method. Also, target typing is preferably realized by providing a gene inspection apparatus using this DNA microarray. The manufacturing method and structure of a DNA microarray and a gene inspection apparatus using the same are well known, so a detailed description thereof will be omitted.

Third Embodiment

In each of the above embodiments, the general approach is to form a specimen solution by amplifying the base sequence of DNA or RNA (cDNA) as an object of examination by using a method such as PCR. In this case, a base sequence present in the specimen is highly likely to contain the base sequence to be examined as its partial sequence. That is, when specimen making which uses an experimental technique such as PCR is performed, the first and second embodiments are especially suitable.

In collectively extracting RNAs present in a cell and measuring the amounts of some of these RNAs, all RNAs present in the cell are base sequences which can react with a formed DNA microarray. The probability that a base sequence to be examined exists in the base sequences of these RNAs or of cDNAs formed from the RNAs is very low.

This will be explained with reference to FIG. 13. In the first and second embodiments, "base sequences which can exist in a specimen or their partial base sequences" and "a base sequence to be examined and its partial base sequences" are substantially identical sets. This set is called a target base sequence in the first and second embodiments. This applies to, e.g., the analysis of genetic DNA indicating human specificity such as MHC.

In contrast, in an experiment for measuring the amount of RNA as described above, the types of base sequences present in a specimen are generally much larger in number than a base sequence to be examined. Accordingly, all base sequences which can exist in the specimen are target base sequences as objects of specificity. The base sequence to be examined is part of these target base sequences.

Figure 13:
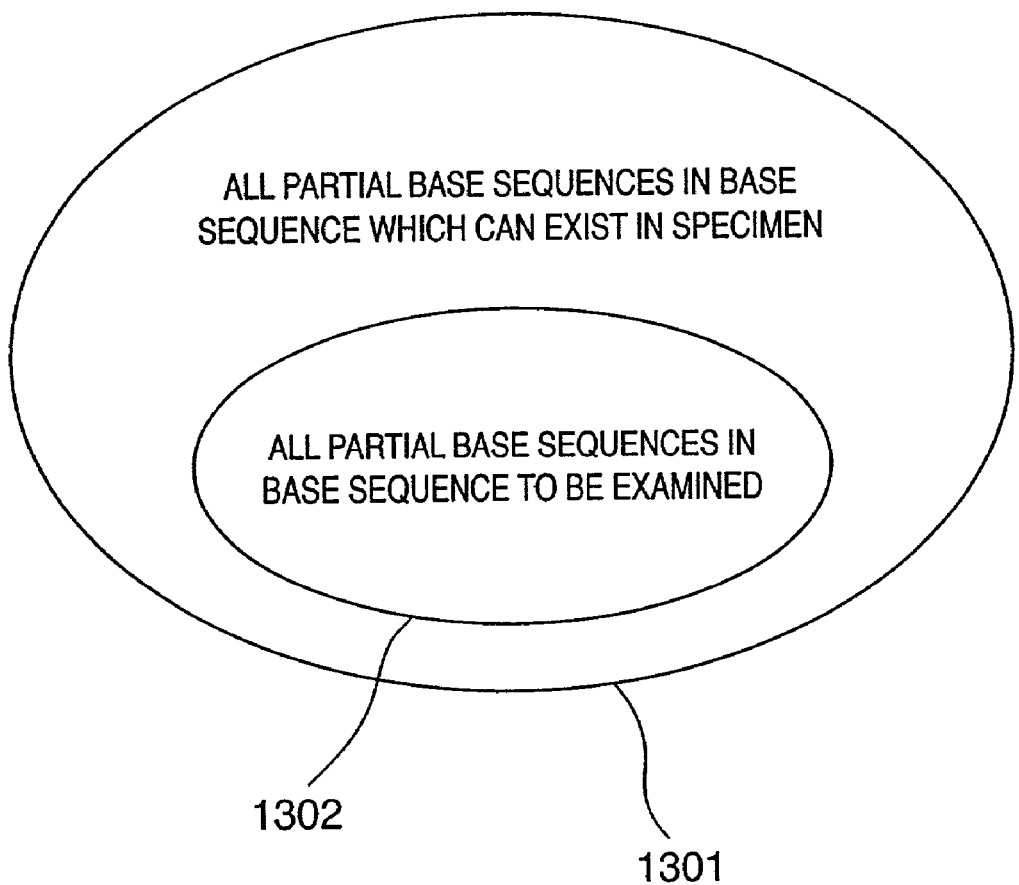
FIG. 13 is a view for explaining the state of base sequence data to which a probe designing method according to the third embodiment is applied.

Referring to FIG. 13, base sequences to be used in the formation of the discrimination tree in the first embodiment or the hash table in the second embodiment are "all partial base sequences in base sequence which can exist in specimen" (1301). The specificity of each partial sequence of the base sequence to be examined is derived on the basis of the specificity of the target base sequence as a whole. In this way, probe candidates are determined.

Figure 14:
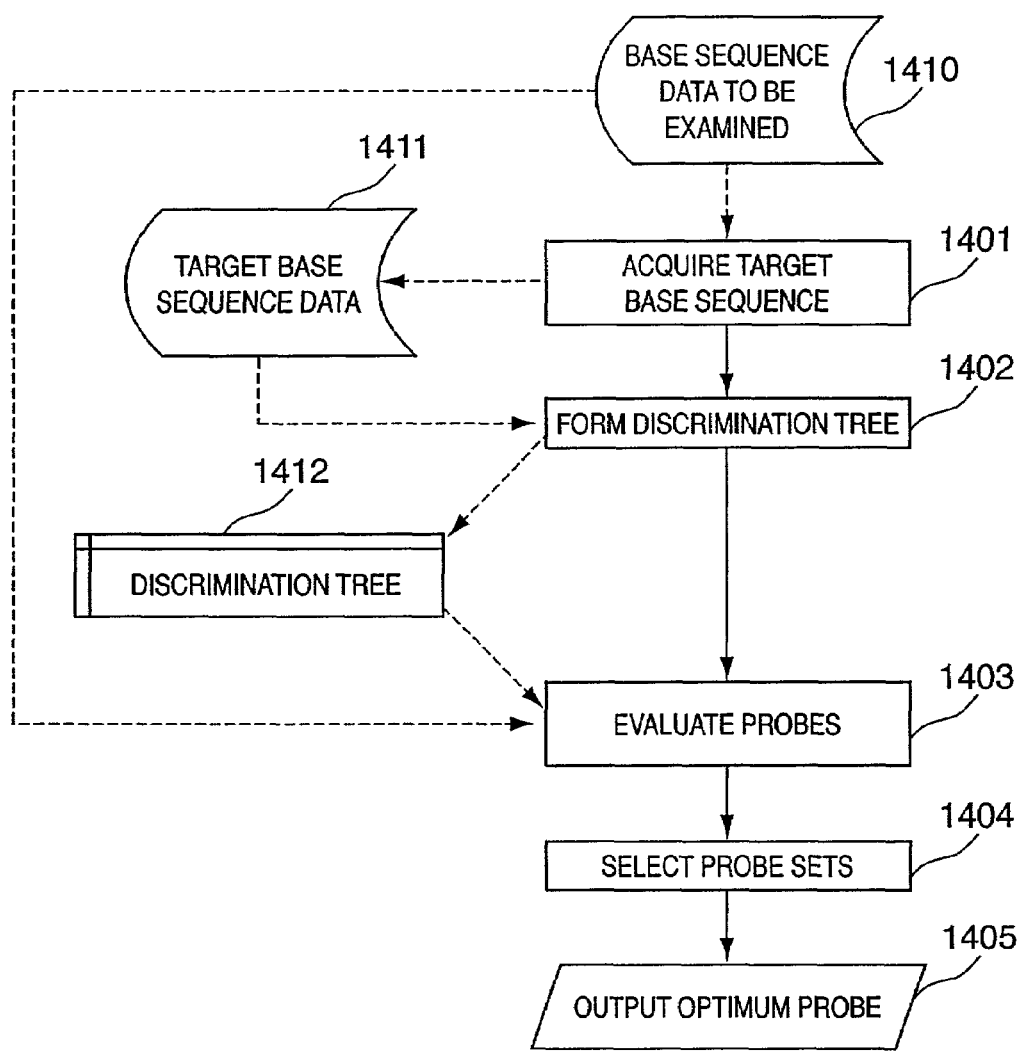
FIG. 14 is a flow chart for explaining a probe designing method using a discrimination tree according to the third embodiment.
Figure 15:
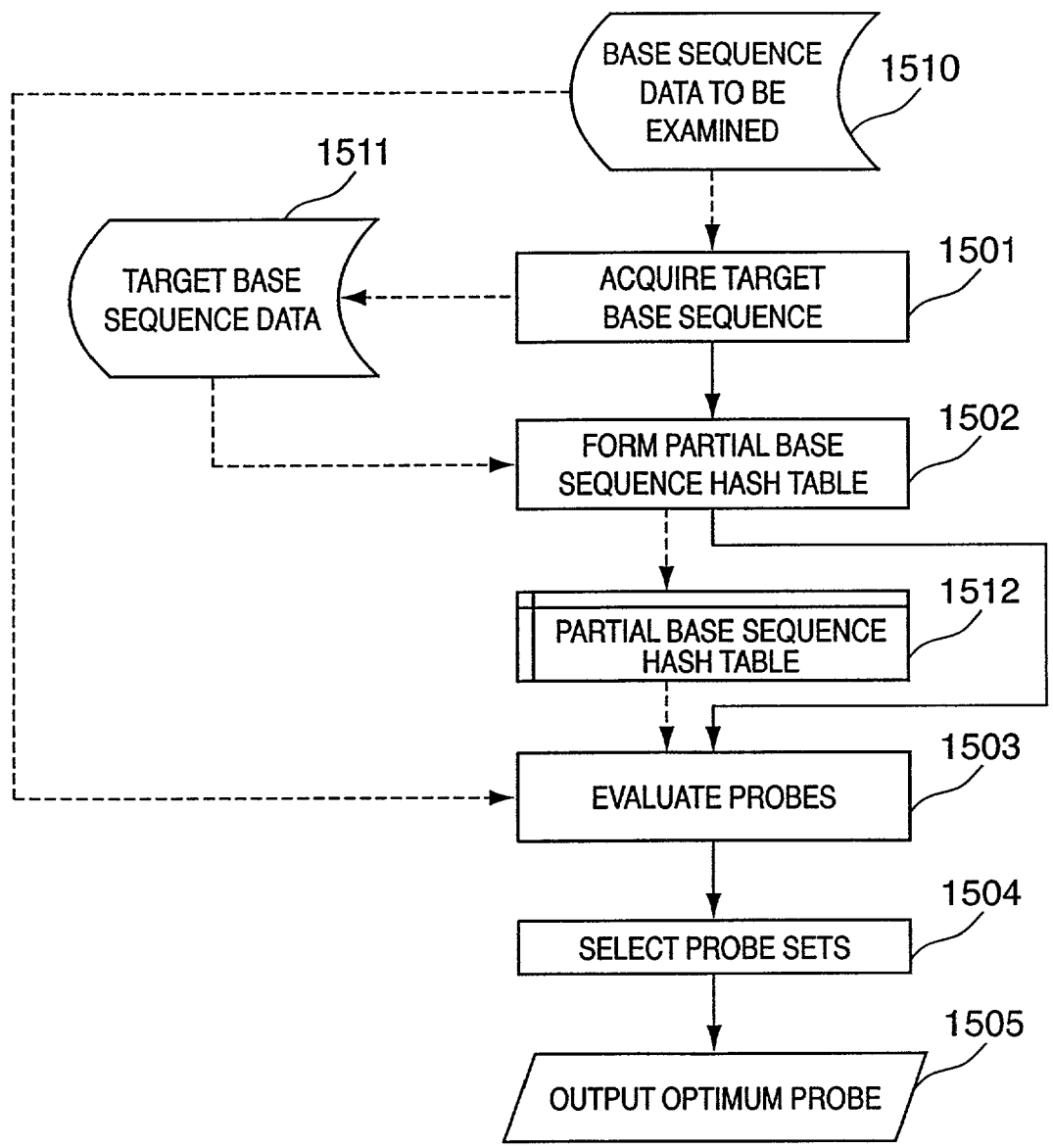
FIG. 15 is a flow chart for explaining a probe designing method using a hash table according to the third embodiment.

The probe designing method according to the third embodiment will be described in detail below with reference to FIGS. 14 and 15.

First, a probe designing procedure using a discrimination tree similar to that in the first embodiment will be explained with reference to FIG. 14. In step S1401, a target base sequence 1411 containing all base sequences which can exist in a specimen is acquired. In this embodiment, a base sequence 1410 to be examined is contained in this target base sequence 1411. Accordingly, this target base sequence 1411 is a base sequence set 1301 containing a base sequence 1302 to be examined as shown in FIG. 13.

In step S1402, a discrimination tree 1412 for typing a plurality of partial base sequences obtained from the target base sequence data 1411 obtained in step S1401 is generated. The generation of this discrimination tree is the same as explained in the first embodiment (steps S102 and S103).

In step S1403, the extent to which each probe candidate present in the discrimination tree 1412 is adequate as a probe is evaluated. The method of this evaluation is also the same as the first embodiment (step S104) except that partial base sequences chosen as probes are selected from partial sequences contained in the base sequence data 1410 to be examined, and that the specificity of each partial base sequence is obtained on the basis of the target base sequence data 1411.

Subsequently, in step S1404, an optimum probe set as a final outcome is selected on the basis of the probe evaluation results in step S1403. This processing is the same as step S105 in the first embodiment. In step S1405, the probe selected in step S1404 is output as an optimum probe. In this embodiment, the input is base sequence data to be examined, and the output is an optimum probe set, or its complementary chain, contained in the base sequence to be examined.

Next, a probe designing method using a hash table similar to that in the second embodiment will be explained with reference to FIG. 15.

In step S1501, a target base sequence 1511 containing all base sequences which can exist in a specimen is acquired. In this embodiment, a base sequence 1510 to be examined is contained in this target base sequence 1511. Accordingly, this target base sequence 1511 is the base sequence set 1301 containing the base sequence 1302 to be examined as shown in FIG. 13.

In step S1502, a partial base sequence hash table 1512 for typing a plurality of partial base sequences obtained from the target base sequence data 1511 obtained in step S1501 is generated. The generation of this partial base sequence hash table 1512 is the same as explained in the second embodiment (steps S1002 and S1003).

In step S1503, the extent to which each probe candidate present in the partial base sequence hash table 1512 is adequate as a probe is evaluated. The method of this evaluation is also the same as the second embodiment (step S1004) except that partial base sequences chosen as probes are selected from partial sequences contained in the base sequence data 1510 to be examined, and that the specificity of each partial base sequence is obtained on the basis of the target base sequence data 1511.

Subsequently, in step S1504, an optimum probe set as a final outcome is selected on the basis of the probe evaluation results in step S1503. This processing is the same as step S1005 in the second embodiment. In step S1505, the probe selected in step S1504 is output as an optimum probe. In this embodiment, the input is base sequence data to be examined, and the output is an optimum probe set, or its complementary chain, contained in the base sequence to be examined.

In this embodiment as described above, it is possible to design a microarray suitable for the purpose of collectively extracting RNAs present in a cell and measuring the amounts of some of these RNAs.

Further, the object of the present invention can also be achieved by supplying a storage medium storing program codes of software for implementing the functions of the above embodiments to a system or an apparatus, and reading out and executing the program codes stored in the storage medium by a computer (or a CPU or MPU) of the system or apparatus.

In this case, the program codes read out from the storage medium implement the functions of the present invention, and the storage medium storing these program codes constitutes the invention.

As this storage medium for supplying the program codes, it is possible to use, e.g., a floppy disk, hard disk, optical disk, magnetooptical disk, CD-ROM, CD-R, magnetic tape, nonvolatile memory card, and ROM.

Also, besides the functions of the above embodiments are implemented by executing the readout program codes by the computer, the present invention includes a case where an OS (Operating System) or the like running on the computer performs part or the whole of actual processing in accordance with designations by the program codes and thereby implements the functions of the above embodiments.

Furthermore, the present invention also includes a case where the program codes read out from the storage medium are written in a memory of a function extension board inserted into the computer or of a function extension unit connected to the computer, and, in accordance with designations by the program codes, a CPU or the like of the function extension board or function extension unit performs part or the whole of actual processing and thereby implements the functions of the above embodiments.

According to the present invention as has been explained above, it is possible to automatically select a probe appropriate for analysis in accordance with a target base sequence to be analyzed, and realize effective support for probe designing.

As many apparently widely different embodiments of the present invention can be made without departing from the spirit and scope thereof, it is to be understood that the invention is not limited to the specific embodiments thereof except as defined in the claims.

What is claimed is:

1. A method of determining and outputting a probe candidate that is utilized for designing a base sequence to be used as a probe which is hybridized with a nucleic acid fragment to perform analysis, comprising:
　　a generation step of generating a tree in which a plurality of partial base sequences obtained on the basis of a plurality of target base sequences are arranged on nodes, said target base sequences including a base sequence to be examined;
　　an extraction step of extracting a partial base sequence indicated by nodes present on a path from one of the nodes to a root node on the tree, the partial base sequence being a portion of the base sequence to be examined;
　　an evaluation step of calculating specificity of the extracted partial base sequence among the plurality of target sequences, evaluating suitability as a probe of the extracted base sequence based on the calculated specificity and obtaining an evaluation result thereof;
　　a determination step of determining a partial base sequence as a probe candidate that is utilized for designing a base sequence to be used as a probe which is hybridized with a nucleic acid fragment to perform analysis on the basis of the evaluation result in the evaluation step; and
　　wherein the evaluation step comprises:
　　calculating the entropy of each node present on the path as the specificity on the basis of the number of times of appearance of a partial base sequence corresponding to the node in the target base sequences;
　　introducing an evaluation function which multiplies a change in the entropy between nodes by a weight which reduces in response to the increase of distance between the center of a partial base sequence and a node; and
　　obtaining an evaluation result based on a calculation result of the evaluation function.

2. The method according to claim 1, wherein the plurality of partial base sequences in the generation step are partial base sequences obtained from a complementary base sequence of the target base sequence.

3. The method according to claim 1, wherein
　　the plurality of partial base sequences in the generation step are partial base sequences obtained from the target base sequence, and
　　the determination step comprises selecting a partial base sequence on the basis of the evaluation result in the evaluation step, and determining a complementary base sequence of the selected partial base sequence as a partial base sequence to be used as a probe.

4. The method according to claim 1, wherein the generation step comprises generating a tree for typing all partial base sequences obtained on the basis of the target base sequence.

5. The method according to claim 1, wherein the evaluation step comprises introducing an evaluation function which, when a base sequence whose specificity with respect to the target changes over a predetermined amount exists at the center of a partial base sequence, gives the partial base sequence an evaluation result to be determined to be used as a probe in the determination step.

6. The method according to claim 5, wherein the determination step comprises determining, as a probe, a partial base sequence corresponding to a node whose value calculated by the evaluation function in the evaluation step exceeds a predetermined value.

7. The method according to claim 1, wherein the determination step comprises determining, as a probe, a partial base sequence corresponding to a node whose change in the entropy exceeds a predetermined value.

8. The method according to claim 1, further comprising the grouping step of grouping the plurality of partial base sequences in accordance with specificity with respect to the target base sequence,
　　wherein the determination step comprises determining a partial base sequence to be used as a probe from each group on the basis of the evaluation result in the evaluation step.

9. The method according to claim 1, further comprising:
　　the grouping step of grouping the plurality of partial base sequences in accordance with specificity with respect to the target base sequence; and
　　the selecting step of selecting a group having specificity appropriate as a probe from groups obtained in the grouping step,
　　wherein the determination step comprises determining a partial base sequence to be used as a probe, from each group selected in the selecting step, on the basis of the evaluation result in the evaluation step.

10. The method according to claim 9, wherein the selecting step comprises eliminating at least a group having no specificity with respect to all targets to be analyzed.

11. The method according to claim 9, wherein the evaluation step comprises evaluating partial base sequences in a group selected in the selecting step.

12. The method according to claim 8, wherein the target contains a plurality of base sequence patterns, and
　　the grouping step comprises assigning, to the same group, partial base sequences which react to the same base sequence patterns.

13. The method according to claim 1, wherein in the tree, the base sequence order of partial base sequences represented by node connections is identified with the base sequence order in the target.

14. The method according to claim 1, wherein in the tree, the base sequence order of partial base sequences represented by node connections is changed such that the central one of corresponding partial base sequences in the target is the first one.

15. The method according to claim 1, wherein the evaluation step comprises evaluating only a partial base sequence having a length within a previously designated range.

16. The method according to claim 1, wherein the evaluation step comprises evaluating only a partial base sequence meeting a melting temperature condition within a previously designated range.

17. The method according to claim 1, wherein the determination step comprises determining a partial base sequence as a probe, from partial base sequences having lengths within a previously designated range, on the basis of the evaluation result in the evaluation step.

18. The method according to claim 1, wherein the determination step comprises determining a partial base sequence as a probe, from partial base sequences meeting a melting temperature condition within a previously designated range, on the basis of the evaluation result in the evaluation step.

19. An information processing apparatus for performing the method of determining a probe candidate that is utilized for designing a base sequence to be used as a probe which is hybridized with a nucleic acid fragment to perform analysis, said apparatus comprising:

generation means for generating a tree in which a plurality of partial base sequences obtained on the basis of a plurality of target base sequences are arranged on nodes, said target base sequences including a base sequence to be examined;

extraction means for extracting a partial base sequence indicated by nodes present on a path from one of the nodes to a root node on the tree, the partial base sequence being a portion of the base sequence to be examined;

evaluation means for calculating specificity of the extracted partial base sequence among the plurality of target sequences, evaluating suitability as a probe of the extracted base sequence based on the calculated specificity and obtaining an evaluation result thereof;

determination means for determining a partial base sequence as a probe candidate that is utilized for designing a base sequence to be used as a probe which is hybridized with a nucleic acid fragment to perform analysis on the basis of the evaluation result in said evaluation means; and wherein said evaluation means calculates the entropy of each node present on the path as the specificity on the basis of the number of times of appearance of a partial base sequence corresponding to the node in the target base sequences, introduces an evaluation function which multiplies a change in the entropy between nodes by a weight which reduces in response to the increase of distance between the center of a partial base sequence and a node, and obtains an evaluation result based on a calculation result of the evaluation function.

20. A storage medium storing a program adapted to control a computer to perform the method of determining a probe candidate according to claim 1.

21. A method of designing a probe including the steps of determining and outputting a probe candidate in accordance with claim 1, and using the probe candidate to design a probe.

* * * * *

UNITED STATES PATENT AND TRADEMARK OFFICE
CERTIFICATE OF CORRECTION

| | |
|---|---|
| PATENT NO. | : 7,254,488 B2 |
| APPLICATION NO. | : 10/081554 |
| DATED | : August 7, 2007 |
| INVENTOR(S) | : Hiroto Yoshii |

It is certified that error appears in the above-identified patent and that said Letters Patent is hereby corrected as shown below:

Title Page, item (56) References Cited, Other Publications, delete "Predicting DNA duple Stability from the base sequence (Proc. Natl. Acad. Sci. USA vol. 83. pp. 3746-3750, Jun. 1986 Biochemistry)." and insert --Predicting DNA duplex Stability from the base sequence (Proc. Natl. Acad. Sci. USA vol. 83, pp. 3746-3750, June 1986 Biochemistry). --

Signed and Sealed this

Twentieth Day of November, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 50
<212> TYPE: DNA
<213> ORGANISM: Homo Sapiens

<400> SEQUENCE: 1
gagcgggtgc ggttgctgga aagatgcatc tataaccaag aggagtccgt                50

<210> SEQ ID NO 2
<211> LENGTH: 50
<212> TYPE: DNA
<213> ORGANISM: Homo Sapiens

<400> SEQUENCE: 2
gagcgggtgc ggttcctgga cagatacttc tatcaccaag aggagtacgt                50

<210> SEQ ID NO 3
<211> LENGTH: 50
<212> TYPE: DNA
<213> ORGANISM: Homo Sapiens

<400> SEQUENCE: 3
gagcgggtgc agttcctgga aagactcttc tataaccagg aggagttcgt                50

<210> SEQ ID NO 4
<211> LENGTH: 50
<212> TYPE: DNA
<213> ORGANISM: Homo Sapiens

<400> SEQUENCE: 4
gagcgggtgc ggttcctgga cagatacttc tataaccagg aggagtccgt                50

<210> SEQ ID NO 5
<211> LENGTH: 49
<212> TYPE: DNA
<213> ORGANISM: Homo Sapiens

<400> SEQUENCE: 5
agcgggtgcg gttgctggaa agatgcatct ataaccaaga ggagtccgt                49

<210> SEQ ID NO 6
<211> LENGTH: 48
<212> TYPE: DNA
<213> ORGANISM: Homo Sapiens

<400> SEQUENCE: 6
gcgggtgcgg ttgctggaaa gatgcatcta taaccaagag gagtccgt                48

<210> SEQ ID NO 7
<211> LENGTH: 47
<212> TYPE: DNA
<213> ORGANISM: Homo Sapiens

<400> SEQUENCE: 7
cgggtgcggt tgctggaaag atgcatctat aaccaagagg agtccgt                47

<210> SEQ ID NO 8
<211> LENGTH: 46
<212> TYPE: DNA
<213> ORGANISM: Homo Sapiens

-continued

```
<400> SEQUENCE: 8
gggtgcggtt gctggaaaga tgcatctata accaagagga gtccgt         46
```